(12) United States Patent
Bringmann et al.

(10) Patent No.: US 6,872,747 B2
(45) Date of Patent: Mar. 29, 2005

(54) DECALACTONES, METHOD FOR MAKING, AND PHARMACEUTICALS THERE FROM

(75) Inventors: Gerhard Bringmann, Würzburg (DE); Peter Prokosch, Jülich (DE); Ru Angelie Edrada, Düsseldorf (DE); Markus Heubes, Kaarst-Buettgen (DE); Sudarsono, Yogyakarta (ID); Eckhard Gunter, Maintal (DE)

(73) Assignee: Biotecmarin GmbH, Mainz (DE)

( * ) Notice: Subject to any disclaimer, the term of this patent is extended or adjusted under 35 U.S.C. 154(b) by 0 days.

(21) Appl. No.: 10/143,596

(22) Filed: May 9, 2002

(65) Prior Publication Data

US 2003/0216354 A1 Nov. 20, 2003

Related U.S. Application Data

(60) Provisional application No. 60/289,876, filed on May 9, 2001.

(51) Int. Cl.[7] .............................................. A61K 31/335
(52) U.S. Cl. .................. 514/450; 514/63; 514/337; 549/214; 549/270; 546/281.7
(58) Field of Search ................ 549/214, 270; 546/281.7; 514/63, 337, 450

(56) References Cited

PUBLICATIONS

Edrada et al, Online analysis of xestodecalactones A–C, novel bioactive metabolites from the fungus *Penicillium cf. montanense* and their subsequent isolation from the sponge *Xestospongia exigua*' Journal of Natural Products (2002), 65(11 1598–1604.*

* cited by examiner

*Primary Examiner*—Amelia A. Owens
(74) *Attorney, Agent, or Firm*—Goodwin Procter, LLP

(57) ABSTRACT

A novel class of decalactones with the general formula (I) and their stereoisomers is disclosed. A method for the synthesis of the decalactones of general formula (I) and the use of the decalactones in pharmaceutical compositions is also described.

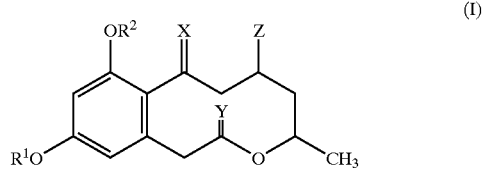

(I)

18 Claims, No Drawings

DECALACTONES, METHOD FOR MAKING, AND PHARMACEUTICALS THERE FROM

This application claims the benefit the U.S. Provisional Application No. 60/289,876 filed on May 9, 2001.

FIELD OF INVENTION

The present invention relates to novel decalactones from marine sponges, method for making the decalactones, and synthetic derivatives thereof.

BACKGROUND OF THE INVENTION

The ocean represents an important source of second metabolites, with its indeterminate number of organisms, such as the bryozoa, mollusca and porifera species. The potential of discovering natural products present in marine sponges and the bacteria, fungi and protists, associated with them, has been explored only to a slight extent. The diversity and structural properties of these natural products can be simulated only at great expense, with classical synthetic methods. An above average number of these natural products have biological properties which are worth following up. Accordingly, they are of interest as potential active ingredients or as novel guiding structures for the development of pharmaceuticals.

Marine sponges require an efficient defense mechanism because of their habitat. It is therefore very likely that highly biologically active compounds can be isolated from these sponges, albeit in very low concentrations. Halichondrin, spongistatin 1, ocadaic acid as well as swinholide A are mentioned as examples of such compounds, which have been successfully isolated from sponges.

The multitude of substances present in extracts of the aforementioned marine organisms require methods for rapidly and intensively differentiating between compounds already known and those which are new. In particular, the "LC triad" is mentioned here which represents a coupling of high performance liquid chromatography (HPLC) with nuclear magnetic resonance (NMR) spectroscopy, mass spectrometry (MS) and circular dichroism (CD) spectroscopy (G. Bringmann et al., ANAL. CHEM. 1998, 70, 2805–2811 and G. Bringmann et al., ANAL. CHEM., 1999, 71, 2678–2686). This method not only permits the identification of known substances directly from the extracts, but also allows for the determination of absolute configuration of structures under suitable circumstance.

The development of tumors is a fundamental disease of higher organisms such as plants, animals and man. The generally recognized multi-step model of carcinosis assumes that due to the accumulation of several mutations in a single cell, the proliferation and differentiation behavior of the cell is changed to such an extent that, after benign intermediate stages, a malignant state with metastasis is attained.

The concept of cancer or tumor includes a syndrome with more than 200 different individual diseases. Tumor diseases can be benign or malignant. The tumors that cause the biggest impact are in the lung, the breast, the stomach, the cervix, the prostate, the head and the neck, the large intestine and rectum, the liver and the blood system. There are large differences with respect to the progression, prognosis and therapy amongst the individual diseases. More than 90 percent of the diagnosed cases relate to solid tumors which can be treated only with difficulty if at all, especially in advanced stages or when the tumor has progressed to metastasis.

The three pillars of combating cancer continue to be surgical removal, radiation and chemotherapy. To date, it has not been possible to develop pharmaceuticals which bring about unambiguous prolongations of survival times or a complete cure in the case of metastasizing solid tumors. It is therefore meaningful to discover new pharmaceuticals for fighting carcinosis.

A new way of treating cancer is the present of signal transduction from a cell surface receptor in the nucleus of the cell by inhibiting specific enzymes. The biological activity can be brought about by synthetic materials and also by natural products.

The search for new anti-infective agents is also meaningful since many diseases caused by infections are inadequately treated resulting in an increase in protozoic and fungal organisms which are resistant to pharmaceuticals commonly used at the present time.

SUMMARY OF THE INVENTION

The compounds of the present invention are denoted by general formula (I):

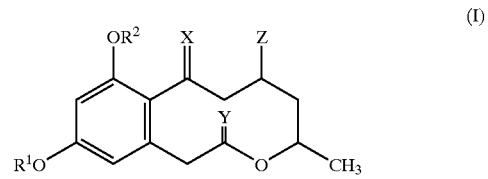

(I)

Wherein $R^1$ is hydrogen; a linear or branched $C_{1-6}$ alkyl, suitably methyl; $C_{1-6}$ alkyl which is mono- or poly-substituted by $C_{6-14}$ aryl, suitably benzyl; linear or branched carboxy $C_{1-18}$ alkyl; linear or branched $C_{1-6}$ alkoxycarbonyl; linear or branched $C_{1-12}$ alkylcarbonyl, suitably acetyl; $C_{2-6}$ alkenyl, suitably allyl; $C_{2-6}$ alkinyl, suitably ethinyl or propargyl; linear or branched cyano $C_{1-6}$ alkyl, suitably cyanomethyl; benzyloxy; 9-fluorenylmethoxycarbonyl (Fmoc); triphenylmethyl (Tr); 2-(4'-pyridyl)ethoxycarbonyl (Pyoc); or diphenylmethylsilyl (DPMS) residues.

$R^2$ is hydrogen; a linear or branched $C_{1-6}$ alkyl, suitably methyl; $C_{1-6}$ alkyl, which is mono- or poly-substituted by $C_{6-14}$ aryl, suitably benzyl; linear or branched carboxy $C_{1-18}$ alkyl; linear or branched $C_{1-6}$ alkoxycarbonyl; linear or branched $C_{1-12}$ alkylcarbonyl, suitably acetyl; $C_{2-6}$ alkenyl, suitably allyl; $C_{2-6}$ alkinyl, suitably ethinyl or propargyl; linear or branched cyano $C_{1-6}$ alkyl, suitably cyanomethyl; benzyloxy; 9-fluorenylmethoxycarbonyl (Fmoc); triphenylmethyl (Tr); 2-(4'-pyridyl)ethoxycarbonyl (Pyoc); or diphenylmethylsilyl (DPMS) residues.

X is O, S, NOH, $NOR^4$, in which $R^4$ is a linear or branched $C_{1-6}$ alkyl, suitably methyl; linear or branched $C_{1-6}$ alkyl, which is mono- or poly-substituted by $C_{6-14}$ aryl, suitably benzyl; linear or branched carboxy $C_{1-18}$ alkyl; linear or branched $C_{1-6}$ alkoxycarbonyl; and linear or branched $C_{1-12}$ alkylcarbonyl, suitably acetyl residues.

Y is O or S, and

Z is H or $OR^3$, in which $R^3$ can be H; a linear or branched $C_{1-6}$ alkyl, suitably methyl; $C_{1-6}$ alkyl, which is mono- or poly-substituted by $C_{6-14}$ aryl, suitably benzyl; linear or branched carboxy $C_{1-18}$ alkyl; linear or branched $C_{1-6}$ alkoxycarbonyl; linear or branched $C_{1-12}$ alkylcarbonyl, suitably acetyl; $C_{2-6}$ alkenyl, suitably allyl; $C_{2-6}$ alkinyl, suitably ethinyl or propargyl; linear or branched cyano $C_{1-6}$ alkyl, suitably cyanomethyl; benzyloxy; 9-fluorenylmethoxycarbonyl (Fmoc); triphenylmethyl (Tr); 2-(4'-pyridyl) ethoxycarbonyl(Pyoc); or diphenylmethylsilyl (DPMS) residues.

When Z is H, the compounds of general formula (I) can be present as R or S enantiomers, or a mixture of R and S enantiomers. Alternatively, when Z is not H but is otherwise defined as above, the compounds of general formula (I) can be present as (R,R), (S,S), (R,S), (S,R) stereoisomers or in the form of all possible mixtures of such stereoisomers.

When $R^1$ and $R^2$ represents H, X and Y are O and Z is H in general formula (I), the compound is named xestodecalactone A. When $R^1$, $R^2$ and $R^3$ and H, X and Y are O, and Z is $OR^3$ in general formula (I), the compounds are named xestodecalactone B or C, depending on the stereochemistry.

The present invention also describes methods for the synthesis of compounds denoted by general formula (I) and the use of such compounds in pharmaceutical compositions.

DETAILED DESCRIPTION OF THE INVENTION

It is an object of the present invention to isolate, characterize (through structure determination), synthesize, and to provide methods of using new biologically active decalactones from associated fungi of marine sponges as pharmaceuticals. The synthetic derivatives of these biologically active decalactones are also contemplated. The compounds of the present invention are to be used as active components of pharmaceuticals. The pharmaceuticals can be used to combat diseases in man and animals.

The new decalactones of the present invention are 10-membered macrolides with a fused 1,3-dihydroxybenzene ring. These natural products were neither synthesized nor isolated from any biological source previous to the work described in this invention. 12-Membered macrolides of the curvularin type have been described from terrestrial strains of *Curvularia* (O. C. Musgrave, J. ORG. CHEM. 1956, 4301–4305), *Penicillium* sp. (S. Lai, Y. Shizuri, S. Yamamura, K. Kawai, Y. Tearda and H. Furukuwa, TETRAHEDRON LETT., 1989, 2241–2244), *Cochliobulus* (E. L. Ghisalberti and C. Y. Rowland, J. NAT. PROD., 1993, 56, 2175–2177) and *Alternaria* (D. J. Roberson and G. A. Strobel, J. NAT. PROD., 1985, 48, 139–141). Other decalactones previously isolated include those from fungi of the diplodia species (K. Wada and T. Ishida, JCS PERKIN I, 1979, 1154–1158) and *Penicillium* (S. Lai, Y. Shizuri, S. Yamamura, K. Kawai, Y. Tearda and H. Furukuwa, TETRAHEDRON LETT., 1989, 2241–2244) and their action as steriod hydroxylase inhibitors described. Likewise, structurally similar lactones can be found in the pathogenic plant fungus *Diplodia pinea* (K. Wada and T. Ishida, JCS PERKIN I, 1979, 1154–1158) and as metabolites in the insect *Phoracanta synonyma* (B. P. Moore and W. V. Brown, AUST. J. CHEM., 1976, 29, 1365–1369). However, the structure and properties of these decalactones differ from those of the compounds described in this invention.

The invention relates to new biologically active decalactones such as those isolated from associated fungi of marine sponges and their synthetic derivatives as pharmaceuticals. The synthesis of this class of compounds is also described.

The new compounds are denoted by general formula (I):

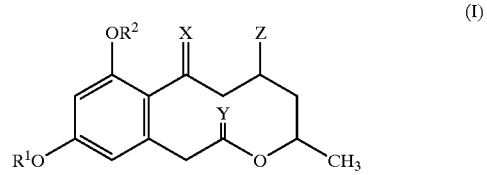

(I)

Wherein $R^1$ is hydrogen; a linear or branched $C_{1-6}$ alkyl, suitably methyl; $C_{1-6}$ alkyl which is mono- or poly-substituted by $C_{6-14}$ aryl, suitably benzyl; linear or branched carboxy $C_{1-18}$ alkyl; linear or branched $C_{1-6}$ alkoxycarbonyl; linear or branched $C_{1-12}$ alkylcarbonyl, suitably acetyl; $C_{2-6}$ alkenyl, suitably allyl; $C_{2-6}$ alkinyl, suitably ethinyl or propargyl; linear or branched cyano $C_{1-6}$ alkyl, suitably cyanomethyl; benzyloxy; 9-fluorenylmethoxycarbonyl (Fmoc); triphenylmethyl (Tr); 2-(4'-pyridyl)ethoxycarbonyl (Pyoc); or diphenylmethylsilyl (DPMS) residues.

$R^2$ is hydrogen; a linear or branched $C_{1-6}$ alkyl, suitably methyl; $C_{1-6}$ alkyl, which is mono- or poly-substituted by $C_{6-14}$ aryl, suitably benzyl; linear or branched carboxy $C_{1-18}$ alkyl; linear or branched $C_{1-6}$ alkoxycarbonyl; linear or branched $C_{1-12}$ alkylcarbonyl, suitably acetyl; $C_{2-6}$ alkenyl, suitably allyl; $C_{2-6}$ alkinyl, suitably ethinyl or propargyl; linear or branched cyano $C_{1-6}$ alkyl, suitably cyanomethyl; benzyloxy; 9-fluorenylmethoxycarbonyl (Fmoc); triphenylmethyl (Tr); 2-(4'-pyridyl)ethoxycarbonyl (Pyoc); or diphenylmethylsilyl (DPMS) residues.

X is O, S, NOH, $NOR^4$, in which $R^4$ is a linear or branched $C_{1-6}$ alkyl, suitably methyl; linear or branched $C_{1-6}$ alkyl, which is mono- or poly-substituted by $C_{6-14}$ aryl, suitably benzyl; linear or branched carboxy $C_{1-18}$ alkyl; linear or branched $C_{1-6}$ alkoxycarbonyl; and linear or branched $C_{1-12}$ alkylcarbonyl, suitably acetyl residues.

Y is O or S, and

Z is H or $OR^3$, in which $R^3$ can be H; a linear or branched $C_{1-6}$ alkyl, suitably methyl; $C_{1-6}$ alkyl, which is mono- or poly-substituted by $C_{6-14}$ aryl, suitably benzyl; linear or branched carboxy $C_{1-18}$ alkyl; linear or branched $C_{1-6}$ alkoxycarbonyl; linear or branched $C_{1-12}$ alkylcarbonyl, suitably acetyl; $C_{2-6}$ alkenyl, suitably allyl; $C_{2-6}$ alkinyl, suitably ethinyl or propargyl; linear or branched cyano $C_{1-6}$ alkyl, suitably cyanomethyl; benzyloxy; 9-fluorenylmethoxycarbonyl (Fmoc); triphenylmethyl (Tr); 2-(4'-pyridyl) ethoxycarbonyl (Pyoc); or diphenylmethylsilyl (DPMS) residues.

When Z is H, the compounds of general formula (I) can be present as R or S enantiomers, or a mixture of R and S enantiomers. Alternatively, when Z is not H but is otherwise defined as above, the compounds of general formula (I) can be present as (R,R), (S,S), (R,S), (S,R) stereoisomers or in the form of all possible mixtures of such stereoisomers.

When $R^1$ and $R^2$ represent H, X and Y are O and Z is H in general formula (I), the compound is named xestodecalactone A. When $R^1$, $R^2$ and $R^3$ are H, X and Y are O, and Z is $OR^3$ in general formula (I), the compounds are named xestodecalactone B or C, depending on the stereochemistry.

The marine sponge *Xestospongia exigua* occurs in the Bali Sea of Indonesia. This sponge was collected and the *Penicillium* sp. fungus was isolated from it. The fungus was cultured and after investigations of the extract with HPLC-MS/MS, HPLC-NMR and HPLC-CD, new natural products were isolated from the culture broth in the form of fungal metabolites. The new compounds isolated are named xestodecalactone A, B and C. The xestodecalactone A, B and C were converted by conventional chemical reactions into new chemical derivatives, which were previously not known.

The compounds of the present invention can be converted with conventional methods into galenic forms, which are suitable for therapeutic applications. Suitable galenic forms of administrations are ointments, drops, tablets, capsules, suppositories, forms suitable for injection, forms suitable for nasal administration and forms suitable for inhalation. The galenic dosage forms can be used intravenously, intramuscularly, intradermally, subcutaneously, intraperitoneally, rectally, topically and intravenously in the form of liposomes.

The invention further comprises a process for the synthesis of compounds of general formula (I) from a biological source. For this purpose, the *Penicillium* sp. fungus is isolated and cultured and compounds are isolated in a suitable manner from the culture broth and purified.

The invention further comprises a process for the synthesis of compounds of general formula (I) from known chemical precursors by conventional chemical reactions. The invention is a meaningful combination of these reactions in accordance with the following synthesis procedure designated herein and in the claims as Synthesis Procedure A.

Synthesis Procedure A suitably of the *Penicillium* sp. strain. The compounds of the invention can also be isolated from other biological sources, especially from other strains of Penicillium.

The fungus of the *Penicillium* sp. occurs in association with a marine sponge *Xestospongia exigua*. The fungus can also occur in other marine sponges. The marine sponge *Xestospongia exigua* can be found in coastal waters of the island of Menganan in the Bali Sea of Indonesia. The marine sponge *Xestospongia exigua*, as a source of the fungus of the *Penicillium* sp., can also occur in other waters. Moreover, the fungus of the *Penicillium* sp. can also occur in other sponges.

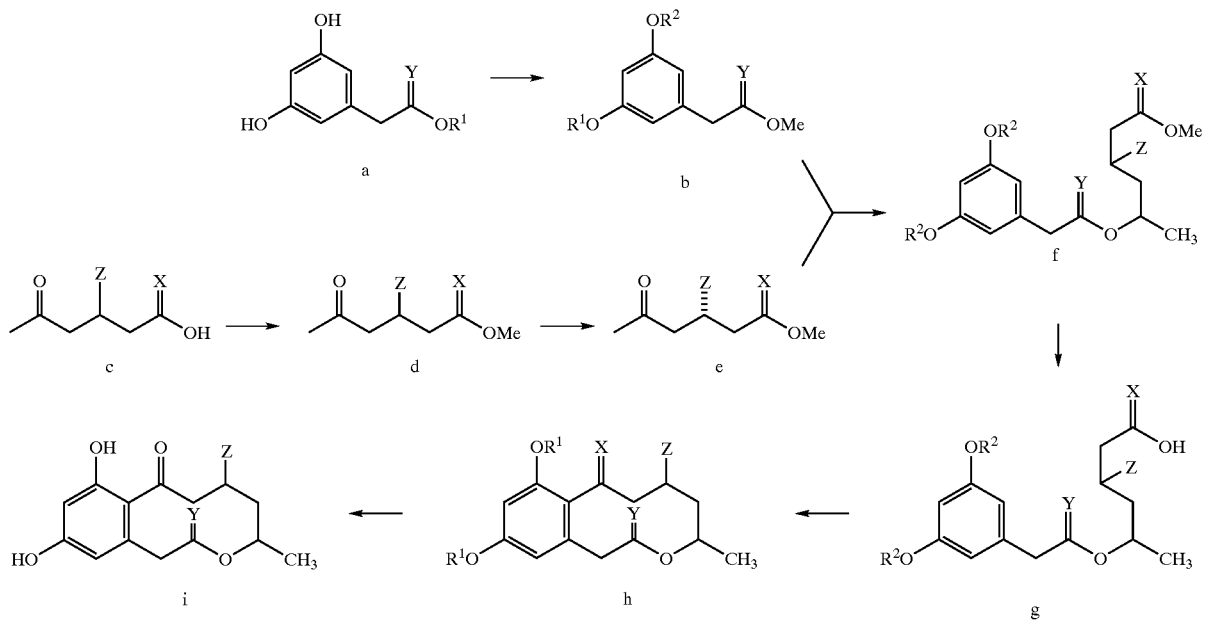

The compounds of the present invention can be used as pharmaceuticals for combating diseases in man or animals. Such diseases include cancers and disorders of the endocrine metabolism inflammatory diseases such as psoriasis, arthritis, Crohn's diseases or asthma. Moreover, the compounds of the present invention can be used for the treatment of infectious diseases such as fungal diseases or diseases due to plasmodia or trypanosomes.

The compounds of the present invention suitably act through interactions of the endogenous proteins, cellular kinases or through hormone receptors, which affect cell metabolism or cell growth. The kinases can be receptors and enzymes of the signal transduction cascade of the cell, such as receptor tyrosine, non-receptor tyrosine and serine threonine kinases. For example, hormone receptors can be coupled to G protein. In addition, an interaction with proteins of the cellular cyto-skeleton is possible such as with tubulin.

It is possible that the compounds of the present invention act through a biological mechanism which was previously unknown. The compounds of the present invention can also kill microorganisms.

EXAMPLES

General Recovery of the Compounds of the Invention from Biological Material

The compounds of the invention are obtained from the mycelia and culture filtrate of a fungus. The fungus is It is also possible to artificially grow the marine sponge containing the fungus of the *Penicillium* sp. in marine aquaculture.

The compounds of the invention are isolated from the culture medium of the fungus of the *Penicillium* sp. by known methods described below. The fungus of the *Penicillium* sp. can also be reproduced and artifically cultured without a sponge.

A strain of the fungus of the *Pencillium* sp. with the register No. HBI-3 is kept at the Alfred Wegener Institute for Polar and Ocean Research in Bremerhaven.

Method of Isolation of Fungus

The fungus of the *Pencillium* sp. is isolated from freshly collected samples of the marine sponge *Xestospongia exigua*. The sponge is collected by divers. Tissue samples are obtained from a portion of the sponge and transferred to suitable culture medium. Agar is suitably used. The incubation is carried out at temperatures between 25° C. and 32° C. The medium used contains nutrients, auxiliary materials and salts, suitably malt abstract and sea salt. The culture is reproduced in the usual manner and pure strains of the *Penicillium* sp. are isolated by re-inoculation on the nutrient medium. Before the extraction, the fungus is permitted to grow in a suitable medium, such as a molt broth medium. After a number of days of incubation, mycelia and culture filtrate are collected and extracted with an organic solvent. Methanol and ethyl acetate are suitably used. Other solvents, such as ethanol, butanol, ether, n-hexane, gasoline, toluene, acetone, methylene chloride, methyl ethyl ketone and t-butyl acetate can also be used. The combined extracts are concentrated to dryness under a vacuum. The contents of the extract are investigated with the help of HPLC-NMR-MS/MS-CD coupling. The crude product thus obtained is separated with the help of a chromatographic method. Suitably, vacuum liquid chromatography is used, but alternative chromatographic procedures may also be employed. Silica is used as stationary phase, but other stationary phases, such as aluminum oxide or cellulose or a separation by liquid chromatography, such as NSCC, are also suitable. A solvent gradient of two or more organic solvents, suitably methylene, chloride and methanol are used but other solvent mixtures, of the combination of 2 or 3 of the following solvents, may also be used: ethanol, propanol, butanol, ether, n-hexane, gasoline, toluene, acetone, ethyl acetate, methyl ethyl ketone, t-butyl acetate. Different fractions are collected and analyzed for their content of the compound of the invention. Suitably, the coupling of HPLC with NMR, NS/NMR MS/MS and CD spectroscopy is used to analyze the mixture. Usually, the compounds of the invention are obtained after the lipophilic components of the abstract. After the fractions of interest are concentrated, the crude product is purified by a chromatographic method on a suitable support material with a solvent gradient. Semi-preparative HPLC, for example, if used as chromatographic method, but purification can also be accomplished by a recrystallization from a suitable solvent or solvent mixture.

EXAMPLES OF COMPOUNDS OF THE INVENTION

The invention is further demonstrated by the following examples.

The fungus of the *Penicillium* sp. is isolated from freshly collected samples of the marine sponge *Xestospongia exigua*. Tissue samples are obtained from the inside of the sponge under sterile conditions and applied on malt agar salt culture. These slant cultures contain malt extract (15 g/L) as well as bay salt (24.4 g/L) and are incubated at 27° C. Pure strains of *Penicillium* sp. are isolated from the growing culture by re-inoculation on malt agar plates. Before the extraction, the fungi are grown in a malt broth medium of 25 g malt extract and one liter of sea water. After 41 days of incubation, the mycelia and culture filtrate are collected and extracted with methanol and ethyl acetate. The combined extracts are concentrated to dryness under vacuum. 6.31 g of crude product is obtained and chromatographed on silica gel with liquid chromatography. A solvent gradient of methylene chloride and methanol is used. The lipophilic fractions 1 to 3 contain fatty acids and steroids, and the xestadecalactones of the present invention are collected infractions 4 to 6. The fractions are concentrated and the crude products are purified by a semi-preparative HPLC (Merck) on a Eurospher C18 column with a methanol gradient of the following composition: 0 minutes 40% MeOH, 30 minutes 60% MeOH, 35–40 minutes 100% MeOH. The compounds of Examples 1 to 3 are obtained.

Example 1

Xestodecalactone A

Colorless powder; $[\alpha]_D$ +28.3° (c 0.31, MeOH)

EIMS (70 eV) m/z $[M]^+$264 (88), $[H-H_2O]^+$246 (22)

Example 2

Xestodecalactone B

Colorless powder; $[\alpha]_D$ +22.5° (c 0.15, MeOH)

EIMS (70 eV) m/z $[M]^+$280 (38)

Example 3

Xestodecalactone C

Colorless powder; $[\alpha]_D$ +17.3° (c 0.3, MeOH)

EIMS (70 eV) m/z $[M]^+$280 (22)

Structural Identification of the Compounds of the Invention

The chemical structures of the claimed compounds are confirmed by modem spectroscopic methods, which include NMR spectroscopy, mass spectrometry and CD spectroscopy.

Synthesis of the Decalactones of the Invention

Aside from being isolated from biological material, the compounds of the present invention can also be produced by chemical synthesis from known starting materials. The compounds may be synthesized by the process shown above in Synthesis Procedure A. The compounds are obtained as racemic mixtures. Alternatively, Compound e (infra) can also be enantioselectively synthesized in any configuration by a selective reducing agent and used for the synthesis of Compound f (infra). In this way, Compound i (infra) can be synthesized in any possible configurations.

Procedure

Example 1

Synthesis Procedure of Xestodecalactone A

Outline of the Synthesis Procedure of Xestodecalactone A:

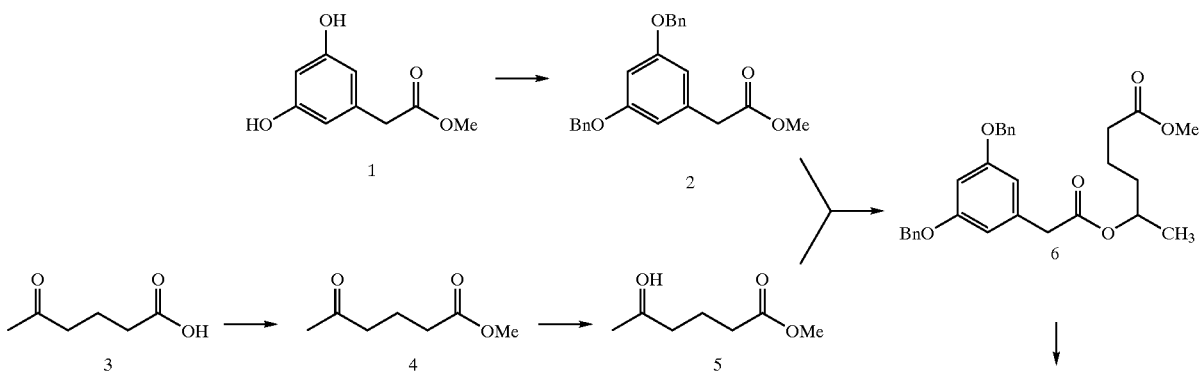

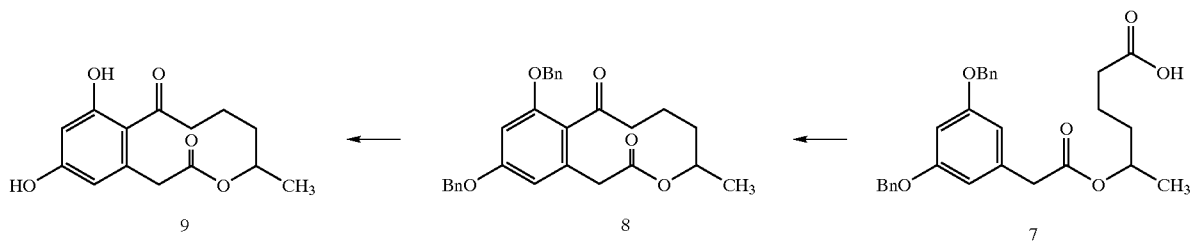

Synthesis of the acetate (Compound 2)

Methyl-(3,5-dihydroxyphenyl) acetate 1 (1 g, 5.6 mmoles), 7 g of potassium carbonate and 7.5 ml of benzyl chloride are heated in 20 mL of acetone until reaction is completed. Subsequently, the inorganic salts are removed by filtration through Celite and the solvent is removed under vacuum. The remaining oil residue is dissolved in 40 mL of 2 N sodium hydroxide, refluxed for 30 minutes and the aqueous phase acidified with 10 N sulfuric acid and extracted with toluene. The organic phase is evaporated to dryness and the residue is recrystallized from ethyl acetate and petroleum ether. 1.66 g (4.7 mmoles) of 2 is obtained which represents a yield of 86%.

Reference: H. Gerlach, HELV. CHIM. ACTA, 1977, 60, 3039–3044.

Synthesis of Methyl-5-hydroxyhexanoate (Compound 4)

5-Hydroxy hexanoic acid 3 (1 g, 7.69 mmoles) is dissolved in 30 mL of methanol, mixed with a catalytic amount of sulfuric acid and heated until the reaction is completed. Subsequently, the solvent is removed under vacuum and the residue distilled under the vacuum of an oil pump. 870 mg (6.00 mmoles) of methyl-5-hydroxyhexanoate 4 is obtained which represents a yield of 78%.

Reference: Organikum Houben-Weyl Method of Organic Chemistry.

Synthesis of Racemic Methyl 5-Hydroxyhexanoate (Compound 5)

Methyl-5-hydroxy hexanoate 4 (0.1 moles) is added at room temperature in portions, with stirring, to a solution of 0.04 moles of $NaBH_4$ in 120 mL of isopropyl alcohol. The reaction mixture is stirred overnight which allows the reaction to run to completion. Dilute hydrochloric acid is then added carefully until hydrogen is no longer evolved. The solution obtained is extracted 5 times with ether. The extract is dried with sodium sulfate and the solvent is distilled off.

Reference: Organikum Houben-Weyl Method of Organic Chemistry.

Synthesis of Compound 6. (analogous to F. Bracher, B. Schulte, LIEBIGS ANN./RECUEIL 1997, 1979–1982).

(3,5)-Dibenzyloxyphenylacetic acid (2, 2.73 g, 7.84 mmoles) and oxalyl chloride (25 mL) are stirred at room temperature under nitrogen for 1 hour. The excess of oxalyl chloride is then removed by vacuum distillation. The residue is dissolved in anhydrous methylene chloride (100 mL), anhydrous potassium carbonate (19 g) and 5 (7.84 mmoles) are added and the mixture is stirred under nitrogen for 6 hours. The precipitate formed is removed by filtration and washed with methylene chloride. The combined filtrates are concentrated under vacuum and the residue is purified by flash chromatography (hexane/ethyl acetate, 8:2). The ester 6 is obtained in this manner.

Synthesis of Compound 7, (analogous to F. Bracher, B. Schulte, LIEBIGS ANN./RECUEIL 1997, 1979–1982).

The compound 6 (6.4 mmoles) is dissolved in the anhydrous triamide of hexamethylphosphoric acid (HMPA, 30 mL) and powdered sodium cyanide (0.945 g, 19.3 mmoles, dried under vacuum at 170° C.) is added. The mixture is stirred for 12 hours at 75° C. cooled, treated with 2 M hydrochloric acid (100 mL, hot) and then extracted with ethyl acetate (2×100 mL). The combined organic phases are washed with water, dried over sodium sulfate and concentrated under vacuum. The residue is purified by flash chromatography (hexane/ethyl acetate 8:2, then ethyl acetate/methanol 9:1). The desired acid 7 is obtained in this manner.

Synthesis of Compound 8, (analogous of H. Gerlach, HELV. CHIM. ACTA, 1977, 60, 3039–3044).

The carboxylic acid 7 (0.59 mmoles) was dissolved in 12 mL of a 2:1 mixture of trifluoroacetic acid and trifluoroacetic anhydride and kept for 2 hours at room temperature. Subsequently, the reagent was removed under vacuum and the residue distributed between benzene and 2 N potassium bicarbonate. After the benzene layers were evaporated, the residue was recrystallized from a mixture of ethyl acetate and hexane.

Synthesis of Compound 9, (analogous to H. Gerlach, HELV. CHIM. ACTA, 1977, 60, 3039–3044).

Dibenzyl ether 8 in 15 mL of a 1:1 mixture of tetradrofuran and methanol was shaken with 25 mg of 10% palladium on charcoal under hydrogen. The catalyst was filtered off, the solvent was removed under vacuum and the residue was recrystallized from a mixture of methanol and benzene.

Other routes are also available for the synthesis of the compounds of the present invention.

Examples 2 and 3

Synthesis Procedure of Xestodecalactone B and C

S-3-hydroxybutyric acid methyl ester is reacted with acetic acid tert-butyl ester in the presence of lithium diisoproylamine (LDA) to form S-5-hydroxy-3-keto-caproic acid tert-butyl esters. Reaction with $NaBH_4$ will stereospecifically reduce the ketone to the R,S- or S,S-3,5-dihydrocaproic acid tert-butyl esters, respectively, which are then converted into the methyl esters. Protection of a hydroxy group and completion of the synthesis follows Synthesis Procedure A.

Synthesis of Derivatives

Derivatives of the class of decalactones can be prepared from the new compounds isolated from the culture of the fungus of the *Penicillium sp* by suitable chemical reactions. These suitable chemical reactions are described in the chemical literature (Organikum, Houben-Weyl Method of Organic Chemistry). These reactions suitably are alkylation reactions, acylation reactions and benzylation of the hydroxy group in the compounds of general formula (I). The oxygen atoms of the ketone and ester carbonyl groups may be replaced, for example, by sulfur.

The derivatization of the compounds of general formula (I) is illustrated by the following Compounds.

Example 4
O-Methyl Derivative

Example 5
O-Benzyl Derivative

Example 6
O-Acetyl Derivative

Biological Properties of the Compounds

The compounds of the present invention have interesting biological properties, which makes them suitable for use as active compounds in pharmaceuticals. In particular, the claimed compounds can be used as agents against carcinoses and as anti-infective agents. The compounds and derivatives inhibit the reproduction of certain strains of yeast, such as *C. albicans* and have fungicidal properties.

Testing of Biological Activity

Testing the biological activity for prevention of the growth of tumor cells is accomplished with the help of conventional commercial XTT testing. For this purpose, different tumor cell lines, such as L 1210, SKOV3 and MCF-7 are used. The effect of the compounds on cell proliferation and on cell count is determined indirectly by their mitochondrial activity. This non-radioactive colorimetric system is based on the test system of Scudiero et al., CANCER RES., 1988, 48, 4827–4833. The basic reaction is the mitochondrial dehydrogenation of the yellow tetrazolium salt XTT into the orange formazan dye. The dehydrogenation takes place only in the active mitochondria and thus correlates with the number of living cells. The formazan dye formed is measured spectrophotometrically at 490 nm and subsequently quantified.

The compounds are used in concentrations of 0.003 μg to 3.16 μg per mL for the testing.

The anti-infective activity is tested by conventional and commercially available test methods.

We claim:

1. A compound of a general formula (I)

wherein $R^1$ is H; a linear or branched $C_{1-6}$ alkyl; $C_{1-6}$ alkyl which is mono -or polysubstituted by a $C_{6-14}$ aryl; linear or branched carboxy $C_{1-18}$ alkyl; linear or branched $C_{1-6}$, alkoxycarbonyl; linear or branched $C_{1-12}$ alkylcarbonyl; $C_{2-6}$ alkenyl; $C_{2-6}$ alkinyl; linear or branched cyano $C_{1-6}$ alkyl; benzyloxy; 9-fluorenylmethoxycarbonyl (Fmoc); triphenylmethyl (Tr); 2-(4'-pyridyl) ethoxycarbonyl (Pyoc); or diphenylmethylsilyl (DPMS) residue, $R^2$ is H; a linear or branched $C_{1-6}$ alkyl; $C_{1-6}$ alkyl which is mono -or polysubstituted by $C_{6-14}$ aryl; linear or branched carboxy $C_{1-18}$ alkyl; linear or branched $C_{1-6}$ alkoxycarbonyl; linear or branched $C_{1-12}$ alkylcarbonyl; $C_{2-6}$ alkenyl; $C_{2-6}$ alkinyl; linear or branched cyano $C_{1-6}$ alkyl; benzyloxy; 9-fluorenylmethoxycarbonyl (Fmoc); triphenylmethyl (Tr); 2-(4'-pyridyl) ethoxycarbonyl (Pyoc); or diphenylmethylsilyl (DPMS) residue, X is O, S, a NOH or $NOR^4$ residue, wherein $R^4$ is a linear or branched $C_{1-6}$ alkyl; $C_{1-6}$ alkyl residue which is mono- or polysubstituted by $C_{6-14}$ aryl; linear or branched carboxy $C_{1-18}$ alkyl; linear or branched $C_{1-6}$ alkoxycarbonyl; or linear or branched $C_{1-12}$ alkylcarbonyl residue, Y is O or S and Z is H or $OR^3$ wherein $R^3$ is H, linear or branched $C_{1-6}$ alkyl; $C_{1-6}$ alkyl residue which is mono- or polysubstituted by $C_{6-14}$ aryl; linear or branched carboxy $C_{1-18}$ alkyl; linear or branched $C_{1-6}$ alkoxycarbonyl; linear or branched $C_{1-12}$ alkylcarbonyl; $C_{2-6}$ alkenyl; $C_{2-6}$ alkinyl; linear or branched cyano $C_{1-6}$ alkyl; benzyloxy; 9-fluorenyl-methoxycarbonyl (Fmoc); triphenylmethyl (Tr); 2-(4'-pyridyl) ethoxycarbonyl (Pyoc); or diphenylmethylsilyl (DPMS) residue.

2. A compound of claim 1, wherein Z is H comprising the R or S enantiomer or a mixture of R and S enantiomers.

3. A compound of claim 2, wherein is a racemic compound.

4. A compound of claim 1, comprising the (R,R), (S,S), (R,S) or (S,R) stereoisomers, or mixtures of the stereoisomers providing that Z is not H.

5. A compound of claim 1 wherein said linear or branched $C_{1-6}$ alkyl residue is methyl, said $C_{1-6}$ alkyl residue substituted by $C_{6-14}$ aryl residue is benzyl, said linear or branched $C_{1-12}$ alkylcarbonyl residue is acetyl, said $C_{2-6}$ alkenyl residue is allyl, said $C_{2-6}$ alkinyl residue is ethinyl or propargyl, and said linear or branched cyano $C_{1-6}$ alkyl residue is cyanomethyl.

6. A compound of claim 1 wherein $R^1$, $R^2$ and Z are each H, X and Y are each O.

7. The compound of claim 6, which is xestodecalactone A.

8. A compound of claim 1, wherein $R^1$, $R^2$ and $R^3$ are all H, X and Y are both O, and Z is $OR^3$.

9. The compound of claim 8, which is xestodecalactone B.

10. The compound of claim 8, which is xestodecalactone C.

11. A pharmaceutical composition containing as an active ingredient a compound of claim 1 as an anti-tumor agent, an anti-infective agent, or a fungicide.

12. A process for treating a tumor, a bacterial or a fungal infection, which comprises administering to a patient in need therefor a pharmaceutical composition of claim 11.

13. A pharmaceutical composition comprising a compound of claim 1 and a pharmaceutically acceptable carrier.

14. A method for preparing the compound of claim 1, comprising the steps of:

esterification of a functionalized compound of formula b

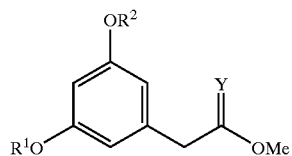

b with an alcohol of formula e

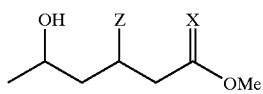

e to produce a compound of formula f

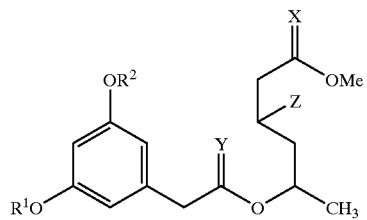

f saponification of the compound of formula f under a basic condition to produce a compound of formula g;

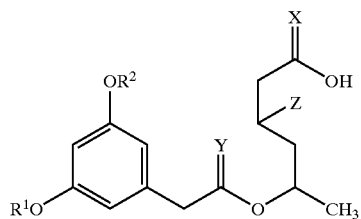

g and acid-catalyzed intramolecular condensation of the compound of formula g to yield the compound according to claim 1.

15. The method of claim 14, further comprising the steps of:

esterification of a 5-ketoacid derivative of formula c

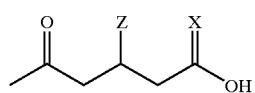

c to produce a 5-ketoacid ester of formula d;

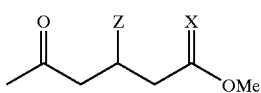

d and reduction of the compound of formula d to produce an alcohol of formula e

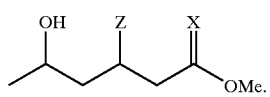

e

16. The method of claim 15, wherein the reduction of the compound of formula d is a enantioselective reduction using a selective reducing agent.

17. The method of claim 14, wherein the compound of formula b is protected with at least one protective group.

18. The method of claim 17, further comprising removal of the at least one protective group following the acid-catalyzed intramolecular condensation.

* * * * *